United States Patent [19]

Kondou

[11] Patent Number: 4,886,677

[45] Date of Patent: Dec. 12, 1989

[54] SURFACE-MODIFIED MESO-ERYTHRITOL COMPOSITION

[75] Inventor: Tsutomu Kondou, Sagamihara, Japan

[73] Assignees: Mitsubishi Kasei Corporation; Nikkon Chemicals Company, Limited, both of Japan

[21] Appl. No.: 235,919

[22] Filed: Aug. 23, 1988

[30] Foreign Application Priority Data

| Aug. 25, 1987 | [JP] | Japan | 62-209364 |
| Oct. 6, 1987 | [JP] | Japan | 62-250756 |
| Oct. 13, 1987 | [JP] | Japan | 62-256262 |
| Oct. 20, 1987 | [JP] | Japan | 62-262709 |
| Dec. 5, 1987 | [JP] | Japan | 62-306858 |

[51] Int. Cl.$^4$ .......................................... A23L 1/236
[52] U.S. Cl. .................................. 426/548; 426/658; 426/660; 426/804; 426/96
[58] Field of Search ............... 426/658, 660, 804, 548, 426/96

[56] References Cited

U.S. PATENT DOCUMENTS

| 4,252,794 | 2/1981 | DuRoss | 426/660 |
| 4,408,041 | 10/1983 | Hirao et al. | 426/660 |
| 4,572,916 | 2/1986 | Lindley et al. | 426/658 |

FOREIGN PATENT DOCUMENTS

9325 4/1980 European Pat. Off. .

OTHER PUBLICATIONS

The Merck Index, "Erythritol", Merck & Co., Rahway, NJ, p. 418, 1968.

*Primary Examiner*—Jeanette Hunter
*Attorney, Agent, or Firm*—Jordan B. Bierman

[57] ABSTRACT

A surface-modified meso-erythritol preparation in the same form as the commercially available sucrose preparations is disclosed. The preparation is less hygroscopic than sucrose preparations, exhibits a beautiful appearance of crystals, or is not solidified under a pressurized condition.

4 Claims, No Drawings

SURFACE-MODIFIED MESO-ERYTHRITOL COMPOSITION

FIELD OF THE INVENTION

This invention relates to surface-modified meso-erythritol preparations and, more particularly, to meso-erythritol preparations, whose surface being modified with water, a non-saccharide sweetening agent, a sugaralcohol or a saccharide, which are in the form of the same commercial sugar preparations now available on the market.

BACKGROUND OF THE INVENTION

Meso-erythritol is a tetrahydric sugaralcohol represented by formula:

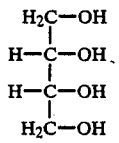

Meso-erythritol crystals are white, have a molecular weight of 122 and a melting point of 119° C., and exhibit high water solubility, non-digestability, and nonbrowning properties.

Meso-erythritol exists in natural algae, mushrooms, etc. and also, in small contents, in Japanese sake, wines, soybean souce, etc. According to organoleptic tests, meso-erythritol has a sweet taste slightly weaker than sucrose and slightly stronger than glucose. Its sweetness corresponds to about 75 to 80% of that of sucrose. It tastes sweet like sucrose but its aftertaste is not so strong as left by sucrose.

Since crystals of meso-erythritol are so hard and brittle, the crystals or edges thereof are easily destroyed during transportation, resulting in deteriorated appearance, which means significant impairment of commercial values.

Meso-erythritol had been isolated from naturally occurring products in a small quantity, but a production process by fertilization has recently been estabilized as disclosed in JP-B-63-9831 (the term "JP-B" as used herein means an "examined published Japanese Patent Application"), JP-A-60-110295 to 110297 (the term "JP-A" as used herein means an "unexamined pablished Japanese patent application"). Further studies are being given to mass production of meso-erythritol.

SUMMARY OF THE INVENTION

As object of this invention is to provide meso-erythritol preparations in the same form as the commercially available sucrose preparations.

More specifically, one object of this invention is to provide meso-erythritol preparations in the form of a compression-molded product.

Another object of this invention is to provide meso-erythritol preparations which do not solidify under pressure.

A further object of this invention is to provide meso-erythritol preparations having an appearance of fine crystals.

It has now been found that the objects of this invention can be accomplished by modifying the surface of meso-erythritol with at least one member selected from the group consisting of water, non-saccharide sweetening agents, sugaralcohols, and saccharides.

DETAILED DESCRIPTION OF THE INVENTION

In one embodiment of the present invention, the surface-modified meso-erythritol preparations in the form of a compression molding can be obtained by compression-molding powders and/or granules of meso-erythritol having a water content of from 0.5 to 5% by weight and drying the molded product. If desired, the powders and/or granules of meso-erythritol may further contain relatively small amounts of other components as hereinafter described.

The meso-erythritol powders to be used may be either crystallized powders or crushed powders of a fused solid and preferably have a particle size through 500 μm sieve of JIS Standard. The meso-erythritol granules to be used preferably have a particle size of smaller than 100 μm. The granules can be prepared by fluidized bed granulation, extrusion granulation and compression granulation, and preferably fluidized bed granulation.

The water content of the powders or granules to be compression-molded should be adjusted to a range of from 0.5 to 5% by weight, preferably from 1 to 2% by weight. If it is too small, the resulting molded products have insufficient hardness to retain their shape. A water content exceeding 5% by weight not only causes oozing of the excess water during drying which leads to disintegration of the molded products but also requires a long time for drying. Adjustment of the water content is conveniently effected by spraying water.

The method of compression molding is not particularly limited. Usual methods of compression molding are preferably employed. The drying of the molded products is preferably at a temperature of from 60° to 100° C. There is no fear as to browning of meso-erythritol during drying as is aroused in the case of sucorse.

In order to examine the mold parting properties, shape-retention before and after the drying, and hardness of meso-erythritol molded products according to this embodiment, meso-erythritol powders having a particle size through 149 μm sieve of JIS Standard were subjected to compression molding with the water content thereof being varied and then dried in hot air of 80° C. The results obtained were as shown in Table 1.

If desired, the meso-erythritol powders or granules to be compression molded may contain other components in relatively small amounts. Such optional components include non-saccharide sweetening agents, extracted coffee liquid, extracted coffee powders, tea powders, fruit juice powders, flavors, souring agents, eutrophics, medical supplies, surface active agents for foodstuff, etc.

In particular, incorporation of a non-saccharide sweetening agent markedly improves sweetness nature of meso-erythritol. For example, a molded product comprising meso-erythritol and a small amount of a non-saccharide sweetening agent, such as Aspartame, Stevioside, saccharin sodum, glycryrrhizin, etc., which leaves sweet aftertaste in the mouth has sweetness closer to sucrose.

TABLE 1

| Water Content | Mold Parting Property | Shape-Retention Before Drying | Shape-Retention After Drying | Hardness of Molded Sugar |
|---|---|---|---|---|
| 0 | good | extremely poor | poor | easy to crumble |
| 0.1 | " | extremely poor | " | easy to crumble |
| 0.2 | " | extremely poor | " | easy to crumble |
| 0.5 | " | good | good | hard |
| 0.8 | " | " | " | " |
| 1.0 | " | " | " | extremely hard |
| 1.5 | " | " | " | extremely hard |
| 2.0 | " | " | " | extremely hard |
| . | . | . | . | . |
| . | . | . | . | . |
| . | . | . | . | . |
| 7.0 | " | " | remarkably crumbled due to oozing of water during drying | hard but easy to crumble |
| 8.0 | " | " | | |
| 9.0 | " | " | | |
| 10.0 | " | " | | |

Combinations of sugaralcohols, e.g., maltitol, sorbitol, xylitol, mannitol, etc., and these non-saccharide sweetening agents have hitherto been known, but it was unknown that sweetness of meso-erythritol can be improved by combining with the non-saccharide sweetening agents.

From the standpoint of improvement on sweetness nature of meso-erythritol, preferred and more preferred weight ratios of the non-saccharide sweetening agents to the meso-erythritol are shown in Table 2. The degrees of sweetness of the resulting combinations are also shown in Table 2, taking that of sucrose as 1.

TABLE 2

| | Non-Sugar Sweetening Agent | | Degree of Sweetness*** (Sucrose = 1) |
|---|---|---|---|
| Kind* | Preferred Weight Ratio to Meso-erythritol** | (More Preferred) | |
| Aspartame | 0.001 to 0.014 | (0.001 to 0.008) | 0.9 to 1.7 |
| Stevioside | 0.0006 to 0.004 | (0.0006 to 0.0024) | 0.9 to 1.7 |
| Saccharine Sodium* | 0.0004 to 0.006 | (0.0004 to 0.001) | 0.9 to 1.3 |
| Glycyrrhizin | 0.0002 to 0.002 | (0.0002 to 0.0009) | 0.7 to 0.9 |

Note:
*The following commercially available products were used.
Aspartame ... produced by Ajinomoto Co., Inc.
Stevioside ... "Chrysanta AX-P" produced by Dai-Nippon Ink & Chemicals, Inc.
Saccharine Na ... produced by Tanabe Seiyaku Co., Ltd.
Glycyrrhizin ... "Licozin A" produced by Ikeda Toka Co., Ltd.
**Product of Nikken Chemicals Co., Ltd. was used
***The degree of sweetness was expressed by a quaotient obtained by dividing a unit weight of sucrose tasting a certain degree of sweetness by a total weight of a mixture of meso-erythritol and the non-saccharide sweetening agent which gives the equal sweetness.

Therefore, for use for coffee, tea, etc., the meso-erythritol can be molded into lumps each having the same degree of sweetness as a commercially available lump of sugar. If desired, the amount of the above-described non-saccharide sweetening agent can be increased to obtain molded products each exhibiting sweetness two or three times that of a commercially available sugar lump.

The molded meso-erythritol preparations according to this embodiment are also characterized by considerably reduced hygroscopicity. This property was proved by determining a water content of the molded meso-erythritol after it was allowed to stand in air at 20° C. and 84% RH for 10 days in comparison with that of a commercially available lump of sugar, a maltitol molded product, or a sorbitol molded product, each having a size of 10×10×10 mm. The result of the determination are shown in Table 3.

TABLE 3

| Molded Sugar | Water Content (20° C., 84% RH, 10 Days) (wt %) |
|---|---|
| commercially available sugar lump | 0.02 |
| meso-erythritol molded preparation of the invention | 0.00 |
| maltitol molded product | 6.0 |
| sorbitol molded product | 20.0 |

The molded preparations of meso-erythritol according to the present invention can also be prepared by compression molding a mixture of meso-erythritol crystal grains and meso-erythritol powders at a mixing weight ratio of from 97/3 to 80/20 having a water content of from 2 to 6% by weight and drying.

The meso-erythritol crystal grains to be used usually have a grain size of from about 0.1 to about 1.5 mm, preferably from 0.2 to 1.0 mm, and the meso-erythritol powders to be used usually have a particle size of not more than 280 μm, preferably not more than 200 μm.

When the above-described mixture of meso-erythritol crystal grains and powders at the specific weight ratio is kneaded in the presence of an appropriate amount of water to have a water content of from 2 to 6% by weight based on the total materials to be molded and then subjected to compression molding, the meso-erythritol powders are filled into gaps among the meso-erythritol crystal grains, and a part of the powders dissolved in water serves as a binder to tightly bind the crystal grains together.

If the weight ratio of the powders to the crystal grains is too small, the strength of the resulting molded sugar would be reduced. If it is too large, the appearance of the molded sugar would be deteriorated due to a small proportion of crystal grains on the surface of the preparations.

If desired, the mixture of the meso-erythritol powders and crystal grains may further contain small amounts of other components. Examples of such optional components include polysaccharides, e.g., gum arabic, tragacanth gum, locust bean gum, guar gum, tamarind gum, pectin, carragenan, xanthane gum, alginic acid, starch, pullulane, dextrin, etc.; gelatin, casein sodium, and fatty acid esters of sucrose. The mixture may furthermore contain, if desired, coffee powders, fruit juice powders, flavors, souring agents, surface active agents, and the like.

In addition, the mixture can contain a non-saccharide sweetening agent for control of degree or nature of sweetness. The non-saccharide sweetening agent includes Aspaltame, Stevioside, Saccharine sodium, glycyrrhizin, Acesulfame potassium, Alitame, etc. Although these non-saccharide sweetening agents per se are inferior in nature of sweetness such that the sweet taste remains in the mouth when taken alone, they are effective to make the taste of the meso-erythritol close to sucrose when combined therewith.

The shape of the molded products according to the present invention is not particularly limited and includes not only a cubic form as is usual but any other shapes, e.g., a spherical form, a tetrahedral form.

Drying of the molded sugar can be carried out by various techniques, such as air drying and vacuum drying. The drying temperature is preferably from 60° to 100° C.

In the preparation of conventional sugar lumps, a blend of granulated sugar (sucrose) and a small amount of a sucrose aqueous solution is molded and dried. Meso-erythritol molded products may be obtained by following this conventional method. That is, meso-erythritol crystal grains are blended with a viscous aqueous solution of various sugars, e.g., sorbitol, maltitol, sucrose, oligosaccharide alcohol, coupling sugar, etc., molded, and dried. However, molded products obtained by such a method are so hygroscopic that they absorb water on standing in air at room temperature, ultimately resulting in the failure of shape retension. Therefore, any means should be taken to prevent water absorption during preservation, for example, by special packaging. To the contrary, since the meso-erythritol molded preparations obtained by the above-described methods do not substantially absorb water, such a special means for protection against water absorption is not required.

In another embodiment of the present invention, surface-modified meso-erythritol preparations which do not undergo solidification even under a pressurized condition can be provided. These preparations can be obtained by coating fine crystals of meso-erythritol with (1) a sweetening component containing a sweetening agent and water, or (2) a sweetening component containing a non-saccharide sweetening agent, a saccharide sweetening agent, and water.

The non-saccharide sweetening agent which can be used for coating includes Aspartame, Stevioside, Saccharin sodium, Alitame, glycyrrhzin, Acesulfame potassium, etc.

The saccharide sweetening agent which may be used in combination with the non-saccharide sweetening agent preferably includes those exhibiting excellent moistureretension, such as reduced straight-chain oligosaccharides, branched oligosaccharide alcohols, sorbitol, coupling sugar, isomerized sugars, maltitol fructose and sucrose.

The fine crystals of meso-erythritol to be coated are not particularly limited in size, but, in usual, preferably have a size of from about 0.1 to about 1.0 mm.

The coating of the meso-erythritol crystals can be carried out by various techniques. For example, an aqueous solution or dispersion (hereinafter inclusively referred to as "aqueous liquid") of the non-saccharide sweetening agent or a mixed aqueous liquid containing the non-saccharide sweetening agent and the saccharide sweetening agent or the non-saccharide sweetening agent and paste, is sprayed onto the crystals; or the above-described aqueous liquid or mixed aqueous liquid is blended with the fine crystals in a kneading machine.

If necessary, the coated fine crystals can be dried by vacuum drying, air drying, and the like, preferably at a temperature of from 60° C. to 100° C.

The surface-modified meso-erythritol preparations have an appearance of crystals like granulated sucrose and can easily be made close to sucrose in degree and nature of sweetness. Further, they are of low calory and do not cause dental caries.

The surface-modified meso-erythritol preparations having an appearance of crystals according to the present invention can also be obtained by coating surfaces of crystal grains of meso-erythritol with a sweetening component containing at least a non-saccharide sweetening agent and a paste.

The sweetening component to be used for coating may further contain the saccharide-sweetening agent.

The non-saccharide sweetening agent which can be used for coating includes Aspartame, Stevioside, Saccharin sodium, Thaumatin, Alitame, glycryrrhizin, Acesulfame potassium, etc.

The saccharide sweetening agent which may be used in combination with the non-saccharide sweetening agent preferably includes those exhibiting excellent moisture-retention, such as reduced straight-chain oligosaccharides, branched oligosaccharide alcohols, sorbitol, coupling sugar, isomerized sugars, and maltitol.

The paste to be used in combination with the non-saccharide sweetening agent includes gelatin, locust bean gum, carrageenan, xanthane gum, pullalane, soluble starch, etc.

The crystals of meso-erythritol to be coated are not particularly limited in size, but, in usual, preferably have a size of from about 0.1 to about 1.0 mm.

The weight ratio of the paste to the non-saccharide sweetening agent usually ranges from 0.05 to 0.3, preferably from 0.1 to 0.2. The paste is usually used as an aqueous solution at a concentration of from 1 to 4% by weight.

The surface-treatment meso-erythritol preparations according to this embodiment have an appearance of crystals like granulated sucrose and can easily be made close to sucrose in degree and nature of sweetness. Further, they are of low calory and do not cause dental caries.

In still another embodiment of the present invention, surface-modified meso-erythritol preparations having a beautiful appearance of crystals are provided, wherein a non-saccharide sweetening agent is contained in individual crystals of meso-erythritol and/or boundaries in aggregated crystals.

The non-saccharide sweetening agent to be incorporated into crystals and/or boundaries thereof includes Asparteme, Stevioside, Saccarin sodium, Thaumatin, Alitame, glycyrrhizin, Acesulfame potassium, etc.

Such meso-erythritol preparations can be obtained typically by crystallization of meso-erythritol from a supersaturated aqueous solution of meso-erythritol to which the non-saccharide sweetening agent has been added. When crystals of meso-erythritol are precipitated from such a supersaturated solution and then allowed to grow, the non-saccharide sweetening agent enters into the individual crystals and/or boundaries of the crystals forming an aggregate. The precipitation continues as long as the meso-erythritol solution is in a supersaturated state. Accordingly, it is desirable to effect crystallization- by cooling a supersaturated aqueous solution of meso-erythritol containing the non-saccharide sweetening agent having a relatively high temperature.

Crystallization of meso-erythritol can be carried out either by a process of allowing the solution to stand or by a fluidized bed process. The former process is suitable for obtaining crystals having a higher content of the non-saccharide sweetening agent. The size of the resulting meso-erythritol crystals and the content of the non-saccharide sweetening agent incorporated vary depending on the degree of supersaturation of the meso-erythritol aqueous solution, the rate of cooling, the stirring conditions, and the like. Therefore, the crystal size or the non-saccharide sweetening agent content can be adjusted to some extent by controlling these factors. The control of the non-saccharide sweetening agent content can also be achieved by adjusting the proportion of the nonsaccharide sweetening agent to meso-erythritol.

Since meso-erythritol can be crystallized from a supersaturated aqueous solution even at a low temperature of 70° C. or less, preparations containing a non-saccharide sweetening agent that undergoes deterioration in degree and nature of sweetness under high temperature, such as Aspartame, can easily be obtained without causing such deterioration. In cases where crystals are precipitated from a meso-erythritol supersaturated aqueous solution at a relatively low temperature over a long period of time, large flat crystals (so-called rock sugar) are obtained. If desired, such large crystals may be crushed to have an appropriate regular size t obtain meso-erythritol preparations having a beautiful appearance of fine crystals.

One example of crystallization by allowing a supersaturated meso-erythritol solution to stand is described below. To a supersaturated aqueous solution of meso-erythritol having a concentration of at least 30%, preferably at least 50%, by weight at a temperature of about 70° C., a non-saccharide sweetening agent, e.g., an Aspartame powder, is added in an amount of from 1 to 1.5% by weight based on the meso-erythritol. Then, the solution about 70° C. is allowed to gradually cool by standing at room temperature to thereby effect crystallization. In this case, a small amount of fine crystals of meso-erythritol may be added as seed crystals, but crystallization is sufficiently induced even in the absence of seed crystals. The saturation concentrations of the meso-erythritol aqueous solution at various temperatures are shown in Table 4 below. The amount of meso-erythritol crystals finally obtained is derived by subtracting the amount corresponding to the saturation concentration of meso-erythritol at the final cooling temperature from the amount contained in the starting supersaturated solution.

TABLE 4

| Temperature | Saturation Concentration |
|---|---|
| (°C.) | (wt %) |
| 80 | 73.2 |
| 60 | 61.8 |
| 40 | 46.8 |
| 20 | 33.2 |

When the degree of supersaturation of the meso-erythritol aqueous solution subject to crystallization is too high, fine crystals are apt to be formed during crystal growth, sometimes resulting in formation of crystals irregular in size. Such being the case, the rate of cooling should be controlled so that the degree of supersaturation may not be excessive.

The thus obtained meso-erythritol preparations have an appearance of crystals like granulated sucrose and can easily be made close to sucrose in degree and nature of sweetness. In addition, the preparations are of low calory and do not cause dental caries.

The present invention will be illustrated in greater detail by way of the following Examples, but it should be understood that the present invention is not deemed to be limited thereto. In these examples, all the percents are by weight unless otherwise indicated.

EXAMPLE 1

One gram of water was sprayed onto 99 g of meso-erythritol powders having a particle size through 125 μm of JIS Standard. After kneading well, the blend was placed in a mod of 10×10×10 cm and molded under a pressure of 20 kg/cm², followed by drying at 80° C. for 10 hours.

The resulting molded sugar and a commercially available lump of sugar of the same size (10×10×10 mm) were allowed to stand in air at 30° C. and 79% RH, and the water absorption was determined with time. The results obtained are shown in Table 5.

TABLE 5

| | Water Content (wt %) | | |
|---|---|---|---|
| | 7 Days | 14 Days | 30 Days |
| Molded sugar of Example 1 | 0.01 | 0.01 | 0.02 |
| Commercially available sugar lump | 0.55 | 0.56 | 0.57 |

It can be seen that the molded sugar according to the present invention does not substantially absorb water even under high temperature and humidity conditions.

EXAMPLE 2

A hundred grams of meso-erythritol powders having a particle size through 149 μm sieve of JIS Standard were mixed well with 0.8 g of Aspartame, and 1.0 g of water was sprayed onto the mixture, followed by kneading well. The blend was press-molded under the same conditions as in Example 1 and dried at 60° C. for 10 hours in vacuo.

When the resulting molded sugar was allowed to stand in air at 30° C. and 79% RH for 30 days, the water absorption was found to be 0.03%. The degree of sweetness of the molded sugar was about 1.5 times that of commerically available sugar.

EXAMPLES 3

Sixty grams of meso-erythritol powders having a particle size through 149 μm of JIS Standard were mixed well with 10 g of water, and 940 g of meso-erythritol crystal grains having a particle size of from 0.2 to 1.0 mm was added thereto, followed by kneading well. The resulting blend was placed in a mold of 8×8×8 mm and press-molded under a pressure of 10 kg/cm² and dried at 90° for 10 hours.

The resulting molded sugar had a beautiful appearance like sugar lump.

For comparison, meso-erythritol molded sugar was prepared by press-molding a mixture of meso-erythritol crystal grains and a sucrose aqueous solution (Comparative Example 1) or a maltitol aqueous solution (comparative Example 2) followed by drying in the same manner as described above.

Each of the molded sugar of Example 3 and the comparative molded sugar was allowed to stand in air at 30° C. and 79% RH for 1 week, and the water absorption was determined. The results are shown in Table 6.

TABLE 6

| Example No. | Water content After 1 Week |
|---|---|
| | (wt %) |
| Example 3 | 0.01 |
| Comparative Ex. 1 | 2.40 |
| Comparative Ex. 2 | 2.00 |

It can be seen that the molded sugar according to example 3 does not substantially absorb water.

EXAMPLE 4

Sixty grams of meso-erythritol powders having a particle size through 149 μm sieve of JIS Standard were mixed well with 4 g of Aspartame, and 30 g of water was added thereto, followed by kneading well. Then, 940 g of meso-erythritol crystal grains (particle size: 0.2 to 1.0 mm) was added thereto, and the mixture was kneaded well. The blend was placed in a mold of 8×8×8 mm, press-molded at a pressure of 10 kg/cm², and dried at 65° C. for 12 hours in vacuo.

The resulting molded sugar had a beautiful appearance like sugar lump. When the molded sugar was allowed to stand in air at 30° C. and 79% RH for 10 days, substantially no water was absorbed.

Then, 5.4 g of the resulting molded sugar was dissolved in 94.6 g of water to prepare an aqueous solution having the same degree of sweetness as a 7% sucrose aqueous solution. As a result of organoleptic testing by 10 female panel members, all the panel members judged the aqueous solution equal or even superior to sucrose in sweetness, such that it was not inferior to sucrose; there was no difference from sucrose; or it was refreshing and rather preferred to sucrose.

EXAMPLE 5

Fifty grams of meso-erythritol powders having a particle size through 149 μm sieve of JIS Standard and 50 g of a 5% carrageenan aqueous solution were mixed well, and 950 g of meso-erythritol crystal grains (particle size: 0.5 to 1.0 mm) was added thereto, followed by kneading well. The resulting blend was placed in a mold of 8×8×8 mm and press-molded under a pressure of 5 kg/cm², followed by vacuum-drying at 80° C. for 12 hours.

The resulting molded sugar had a beautiful appearance like sugar lump. When it was allowed to stand in air at 30° C. and 79% RH for 10 days, it absorbed substantially no water.

Further, moldability of the above-described blend was proved more satisfactory than in the case of using 50 g of water in place of the carrageenan aqueous solution with the other conditions being the same.

EXAMPLE 6

To 670 g of crystal grains of meso-erythritol (particle size: 0.1 to 1.0 mm) was added an aqueous liquid containing 1.4 g of stevioside dispersed and then dissolved in 35 g of water, and the mixture was kneaded well in a kneader. The blend was completely dried by air at 80° C. The resulting preparation had a beautiful appearance of crystals like granulated sucrose. It was of low calory and was causative of no dental caries. The results of organoleptic testing by 15 panel members were as shown in Table 7 below. The preparation was proved markedly superior in sweetness to preparations of Stevioside alone.

TABLE 7

| Preparation | Sweetening Component (Concn.) | | Results of Evaluation on Sweetness by 15 panel Members |
|---|---|---|---|
| | Stevioside | Erythritol | |
| | (wt %) | (wt %) | |
| Preparation of Example 6 (6.714 g of the preparation dissolved in water to make 100 g)* | 0.014 | 6.7 | (1) sweetness close to sucrose (2) mild sweetness (3) no aftertaste left |
| Preparation of Stevioside alone (0.059 g of Stevioside dissolved in water to make 100 g)** | 0.059 | 0 | (1) irritating sweetness and bitterness (2) drug-like taste and astrictive (3) sweet aftertaste left |

Note: *, **The degree of sweetness of both the aqueous solutions corresponded to that of about 7% sucrose aqueous solution.

EXAMPLE 7

Aspartame (2.2 kg) was kneaded well with 10.8 kg of a reduced straight chain oligosaccharide aqueous solution (concentration: about 70%), and 540 kg of meso-erythritol crystal grains (particle size: 0.1 to 0.5 mm) was added thereto, followed by kneading well in a kneader.

The resulting meso-erythritol preparation having coated with a mixed sweetening component of Aspartame and reduced straight chain oligosaccharide had a beautiful appearance of crystals like granulated sucrose. It was of low calory and no cariogenic.

A 500 g portion of the resulting preparation was packed in a polyethylene bag of 150 mm in width, 196 mm in length an 60 μm in thickness, and the opening was sealed. The bag was put in a three-layered kraft paper bag commonly employed for sucrose packaging, and the opening was run up on a sewing machine.

For comparison, 500 g of crystal grains of mesoerythritol (particle size: 0.1 to 0.5 mm) was packed in the same manner as described above.

Each of these bags were placed on a pallet in a warehouse. An iron plate of 150 mm×200 mm×3 mm was put on the bag, and a 10 kg weight was further put thereon. After leaving the bag to stand at room temperature for one month, the content of the bag was taken out therefrom. The meso-erythritol crystals were found to have been solidified as a whole, while the preparation of Example 7 had not underwent such solidification at all.

EXAMPLES 8 TO 12

Each of sorbitol in example 8, maltitol in example 9, coupling sugar in example 10, isomerized sugar in example 11, and an acid- or enzyme-hydrolyzate of starch in example 12, was dissolved in water to prepare an aqueous solution having a solid content of 75%.

A mixture of 25 kg of the aqueous solution, 2.2 kg of Aspartame, and 540 kg of meso-erythritol (particle size: not more than 0.5 mm) was throughly blended in a kneader in the same manner as in Example 6.

The resulting meso-erythritol preparation was packed and tested in the same manner as in Example 7. As a result, it was found that the preparation had not been solidified at all.

EXAMPLE 13

A mixture of 2.2 g of Aspartame (produced by Ajinomoto Co., Inc.) and 30 g of a 1% aqueous solution of gelatin ("#200" produced by Nitta Gelatin Co., Ltd.) was blended well and heated at 70° C. In a fluidized bed granulating drier was charged 540 g of crystal grains of meso-erythritol (particle size: 0.1 to 1.0 mm). While the grains were made to flow, the above-prepared mixture of Aspartame and gelatin was sprayed thereon, followed by drying at 70° C.

In the resulting sweet preparation, it was found that the meso-erythritol crystals were surely coated with Aspartame with the aid of gelatin having a strong binding property. The preparation exhibited a beautiful appearance like granulated sugar. Further, the sweet taste of the preparation was evaluated by organoleptic testing by 15 panel members. The results obtained are shown in Table 8. It can be seen from Table 8 that the preparation was considerably superior to Aspartame alone.

TABLE 8

| Preparation | Sweetening Component (Concn.) | | | Results of Evaluation on Sweetness by 15 Panel members |
|---|---|---|---|---|
| | Aspartame (wt %) | Gelatin (wt %) | Meso-Erythritol (wt %) | |
| Preparation of Example 13 (5.425 g of the preparation dissolved in water to make 100 g)* | 0.022 | 0.003 | 5.4 | (1) sweetness close to sucrose (2) mild sweetness (3) no aftertaste left |
| Preparation of Aspartame aloe (0.059 g of Aspartame dissolved in water to make 100 g)** | 0.059 | 0 | 0 | (1) irritating sweetness and bitterness (2) drug-like taste and astrictive taste |

Note:
*, **The degree of sweetness of both the aqueous solutions corresponded to that of about 7% aqeous solution.

EXAMPLES 14 TO 18 AND COMPARATIVE EXAMPLE 3

A sweet preparation was prepared in the same manner as in Example 13, except for changing the composition of the sweetening component as shown in Table 9 below.

TABLE 9

| Example No. | Sweetening Component |
|---|---|
| 14 | Asparatame (2.2 g) + 1% aqueous solution of locust beam gum (30 g) |
| 15 | Asparatame (2.2 g) + 1% aqueous solution of carrageenan 930 g) |
| 16 | Asparatame (2.2 g) + 1% xanthane gum aqueous solution (30 g) |
| 17 | Asparatame (2.2 g) + 1% pullalane aqueous solution (30 g) |
| 18 | Asparatame (2.2 g) + 1% soluble starch aqueous solution (30 g) |

Comparative Asparatame (2.2 g) + water (30 g) Example 3
Note: The materials used were purchased from the following makers:
Aspartame: Ajinomoto Co., Inc.
Raw Castor Bean gum: San-ei Kagaku Co., Ltd.
Carrageenan: Mitsubishi Acetate Co., Ltd. ("MV-300")
Xanthan Gum: Dainippon Pharmaceutical Co., Ltd.

Comparative Asparatame (2.2 g) + water (30 g) Example 3

Note: The materials used were purchased from the following makers:
Aspartame: Ajinomoto Co., Inc.
Raw Castor Bean gum: San-ei Kagaku Co., Ltd. Carrageenan: Mitsubishi Acetate Co., Ltd. ("MV-300")
Xanthan Gum: Dainippon Pharmaceutical Co., Ltd.
Pullulane: Hayashibara Co., Ltd.
Soluble Starch: Wako Pure Chemical Ind., Ltd.

Each of the above prepared meso-erythritol preparations of Examples 14 to 18 had a beautiful appearance like granulated sugar, whereas the crystals of meso-erythritol of Comparative Example 3 were not sufficiently coated with the sweetening component and inferior in appearance.

EXAMPLE 19

A 50% aqueous solution containing 400 g of meso-erythritol was prepared and kept at 70° C. To the solution was added 4, 8, or 10 g of Aspartame powders, followed by thoroughly mixing. The mixture was gradually cooled by allowing to stand at room temperature for 8 hours thereby allowing crystals to grow. The crystals thus precipitated were separated from the mother liquor.

The sugar liquid attached on the surface of the crystals was washed away with a 70% alcohol aqueous solution at 5° C. and then dried at 60° C. for 5 hours in vacuo. The Asparatame content in the resulting crystals was as shown in Table 10.

TABLE 10

| Amount of Asparatame (g) | Asparatame Content in Crystals (wt %) |
|---|---|
| 4 | 0.1 |
| 8 | 0.1 |
| 10 | 0.2 |

Each of the resulting meso-erythritol crystals containing Asparatame had a beautiful crystal appearance.

EXAMPLE 20

A 50% aqueous solution containing 400 g of mesoerythritol was prepared and kept at 70° C. To the solution was added 4, 8, or 10 g of Saccharin sodium powders, followed by thoroughly mixing. The mixture was gradually cooled by allowing to stand at room temperature for 8 hours thereby allowing crystals to grow. The crystals thus precipitated were separated from the mother liquor.

The sugar liquid attached on the surface of the crystals was washed away with a 70% alcohol aqueous solution at 5° C. and then dried at 80° C. for 2 hours.

The content of Saccharin sodium in the resulting crystals was as shown in Table 11.

TABLE 11

| Amount of Saccharin Sodium (g) | Saccharin Sodium Content in Crystals (wt %) |
|---|---|
| 4 | 0.15 |
| 8 | 0.17 |
| 10 | 0.25 |

Each of the resulting meso-erythritol crystals containing Saccharin sodium had a beautiful crystal appearance.

While the invention has been described in detail and with reference to specific embodiments thereof, it will be apparent to one skilled in the art that various changes and modifications can be made therein without departing from the spirit and scope thereof.

What is claimed is:

1. A surface-modified meso-erythritol composition obtained by mixing meso-erythritol crystal grains and meso-erythritol powders in a weight ratio of from 97/3 to 80/20, adding water to the resulting mixture to adjust to a water content of from 2 to 6% by weight, kneading the mixture, compression-molding the mixture, drying the resulting molded product.

2. A surface-modified meso-erythritol composition as in claim 1, wherein said mixture of meso-erythritol crystal grains and meso-erythritol powders further contains relatively small amounts of other components.

3. A surface-modified meso-erythritol composition as in claim 4 obtained by coating surfaces of meso-erythritol crystal grains with a sweetening component containing a non-saccharide sweetening agent.

4. A surface-modified meso-erythritol composition as in claim 1 obtained by coating surfaces of meso-erythritol crystal grains with a sweetening component containing a non-saccharide sweetening agent and water.

* * * * *